United States Patent
Yates et al.

(10) Patent No.: US 9,050,100 B2
(45) Date of Patent: Jun. 9, 2015

(54) SURGICAL INSTRUMENT WITH FEEDBACK AT END EFFECTOR

(71) Applicant: Ethicon Endo-Surgery, Inc., Cincinnati, OH (US)

(72) Inventors: David C. Yates, Hillsboro, OH (US); Frederick E. Shelton, IV, Hillsboro, OH (US); Kevin L. Houser, Springboro, OH (US); Aron O. Zingman, Cambridge, MA (US); Donna L. Korvick, Maineville, OH (US); Ashvani K. Madan, Mason, OH (US); John W. Willis, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 136 days.

(21) Appl. No.: 13/709,420

(22) Filed: Dec. 10, 2012

(65) Prior Publication Data

US 2014/0163549 A1    Jun. 12, 2014

(51) Int. Cl.
  *A61B 18/18*  (2006.01)
  *A61B 18/14*  (2006.01)
  *A61B 17/00*  (2006.01)
  *A61B 18/00*  (2006.01)

(52) U.S. Cl.
  CPC ..... *A61B 18/1445* (2013.01); *A61B 2017/0003* (2013.01); *A61B 2017/00084* (2013.01); *A61B 2017/00128* (2013.01); *A61B 2017/00473* (2013.01); *A61B 2018/00303* (2013.01); *A61B 2018/00607* (2013.01); *A61B 2018/0063* (2013.01); *A61B 2018/0066* (2013.01); *A61B 2018/00809* (2013.01); *A61B 2018/00827* (2013.01); *A61B 2018/1455* (2013.01); *A61B 2018/1495* (2013.01); *A61B 2017/00115* (2013.01)

(58) Field of Classification Search
  USPC .......................................................... 606/52
  See application file for complete search history.

(56) References Cited

U.S. PATENT DOCUMENTS 6,500,176 B1   12/2002   Truckai et al.
6,783,524 B2   8/2004   Anderson et al.
(Continued)

FOREIGN PATENT DOCUMENTS

EP    1 880 687       1/2008
EP    2 425 871       3/2012
WO    WO 2004/071278  8/2004

OTHER PUBLICATIONS

International Search Report dated Jun. 27, 2014 for Application No. PCT/US2013/073778.
(Continued)

*Primary Examiner* — Robert N Wieland
(74) *Attorney, Agent, or Firm* — Frost Brown Todd LLC

(57) ABSTRACT

An apparatus for operating on tissue includes a body, a lip in communication with the body, and at least one electrode also in communication with the body. The body is able to mechanically couple with a portion of an end effector, which may be controlled by a user through a handpiece. The lip is configured to grip a portion of the end effector. The at least one electrode is configured to provide sufficient electrical energy to weld at least a portion of tissue. In some versions, a temperature sensitive material may be positioned on a portion of the end effector. Additionally, in some versions, the handpiece of the end effector may comprise feedback features able to convey information to the user.

20 Claims, 13 Drawing Sheets

(56) References Cited

U.S. PATENT DOCUMENTS

| | | |
|---|---|---|
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 2011/0087218 A1 | 4/2011 | Boudreaux et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |
| 2013/0247343 A1* | 9/2013 | Horner et al. ............. 29/25.35 |

OTHER PUBLICATIONS

U.S. Appl. No. 13/709,473, filed Dec. 10, 2012.
U.S. Appl. No. 61/410,603, filed Nov. 5, 2010.
International Written Opinion dated Jun. 27, 2014 for Application No. PCT/US2013/073778.

* cited by examiner

SURGICAL INSTRUMENT WITH FEEDBACK AT END EFFECTOR

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. patent application Ser. No. 13/622,729, entitled "Surgical Instrument with Multi-Phase Trigger Bias," filed Sep. 19, 2012, published as U.S. Pub. No. 2013/0030428 on Jan. 31, 2013, the disclosure of which is incorporated by reference herein; and U.S. patent application Ser. No. 13/622,735, entitled "Surgical Instrument with Contained Dual Helix Actuator Assembly," filed Sep. 19, 2012, published as U.S. Pub. No. 2013/0023868 on Jan. 24, 2013, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
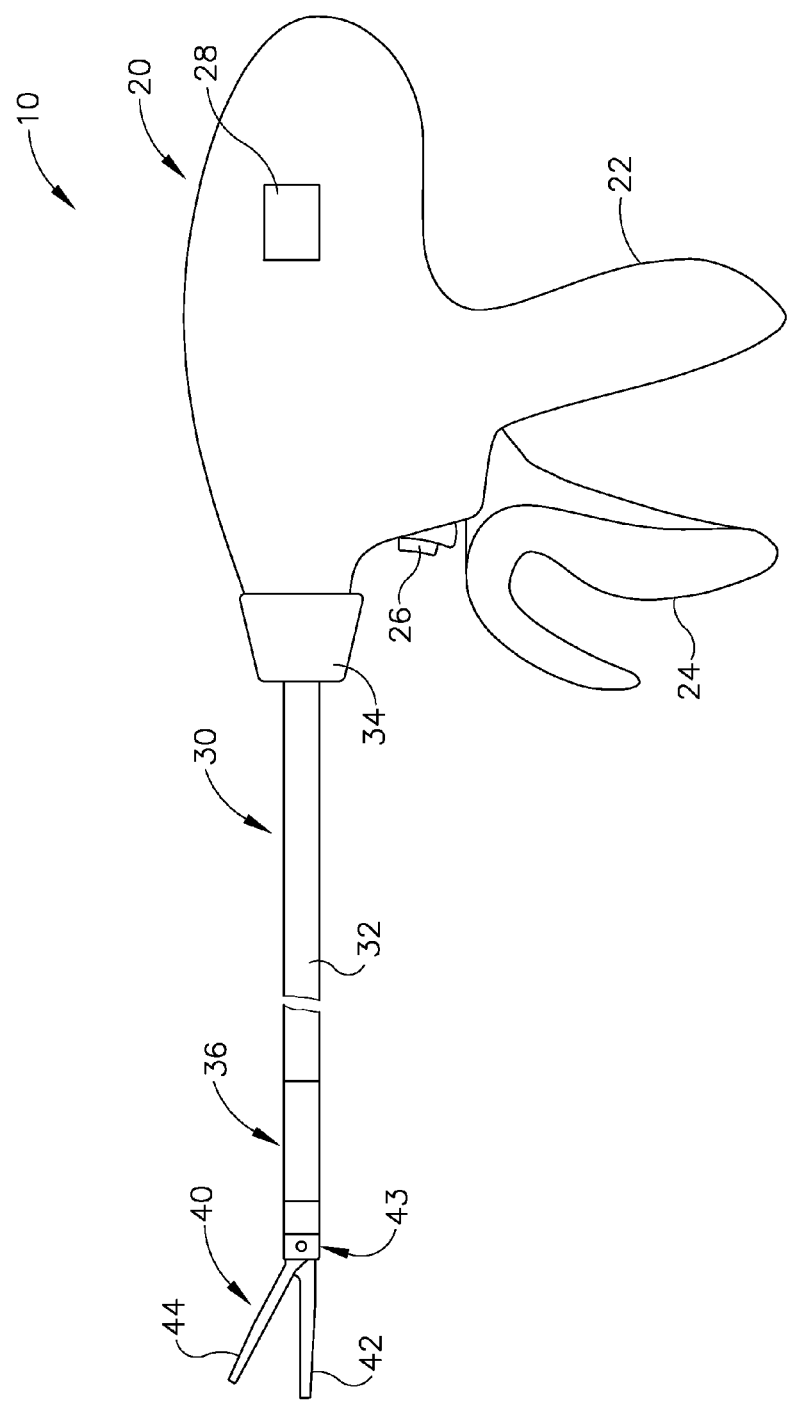
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device With Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, now U.S. Pat. No. 8,939,974; U.S. Pub. No. 2012/0116379; U.S. Pub. No. 2012/0078243; U.S. Pub. No. 2012/0078247; U.S. patent application Ser. No. 13/622,729, published as U.S. Pub. No. 2013/0030428; and/or U.S. patent application Ser. No. 13/622,735, published as U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. patent application Ser. No. 13/622,735, published as U.S. Pub. No. 2013/0023868 on Jan. 24, 2013, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
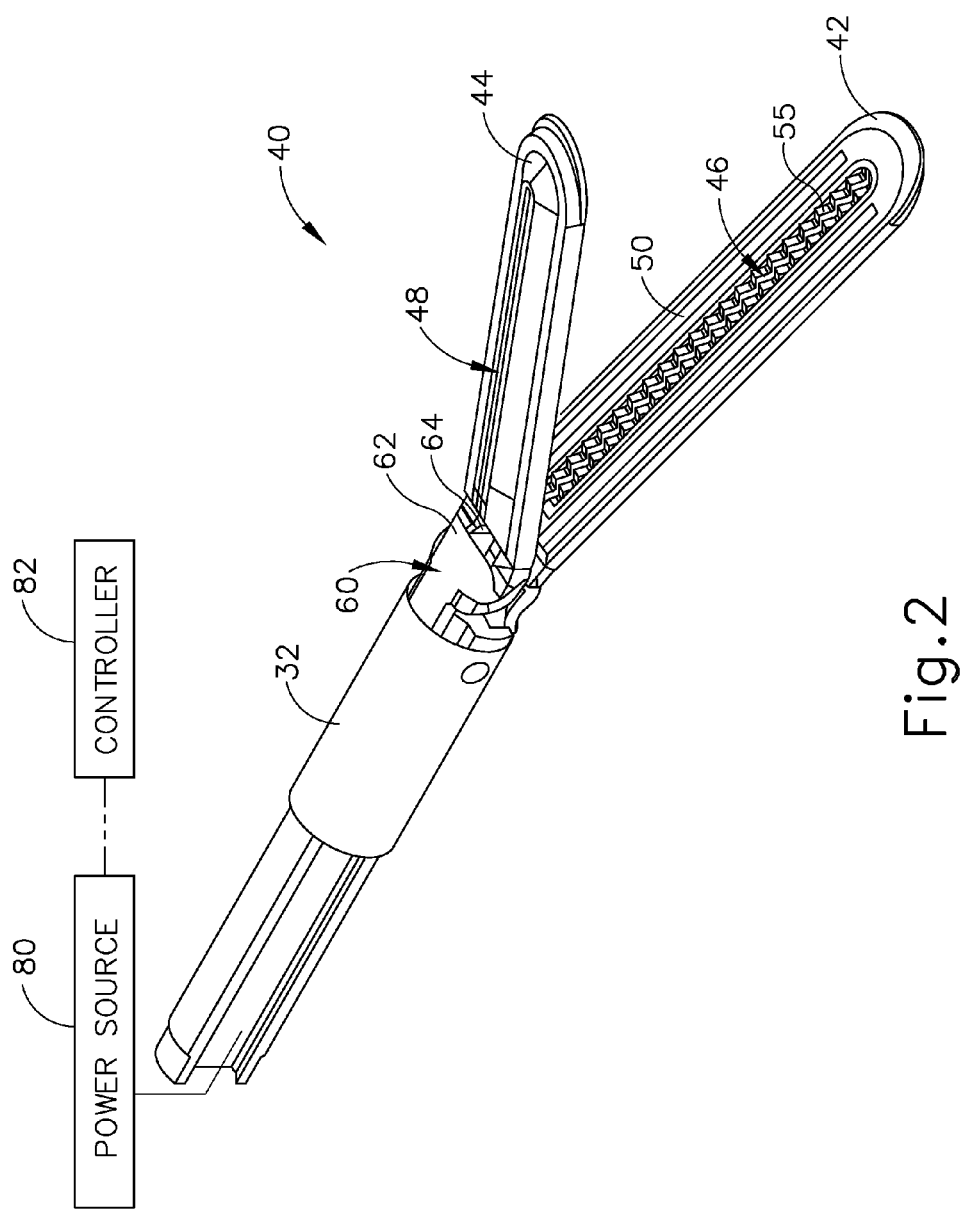
FIG. 2 depicts a perspective view of the end effector of the instrument of FIG. 1, in an open configuration.
Figure 3:
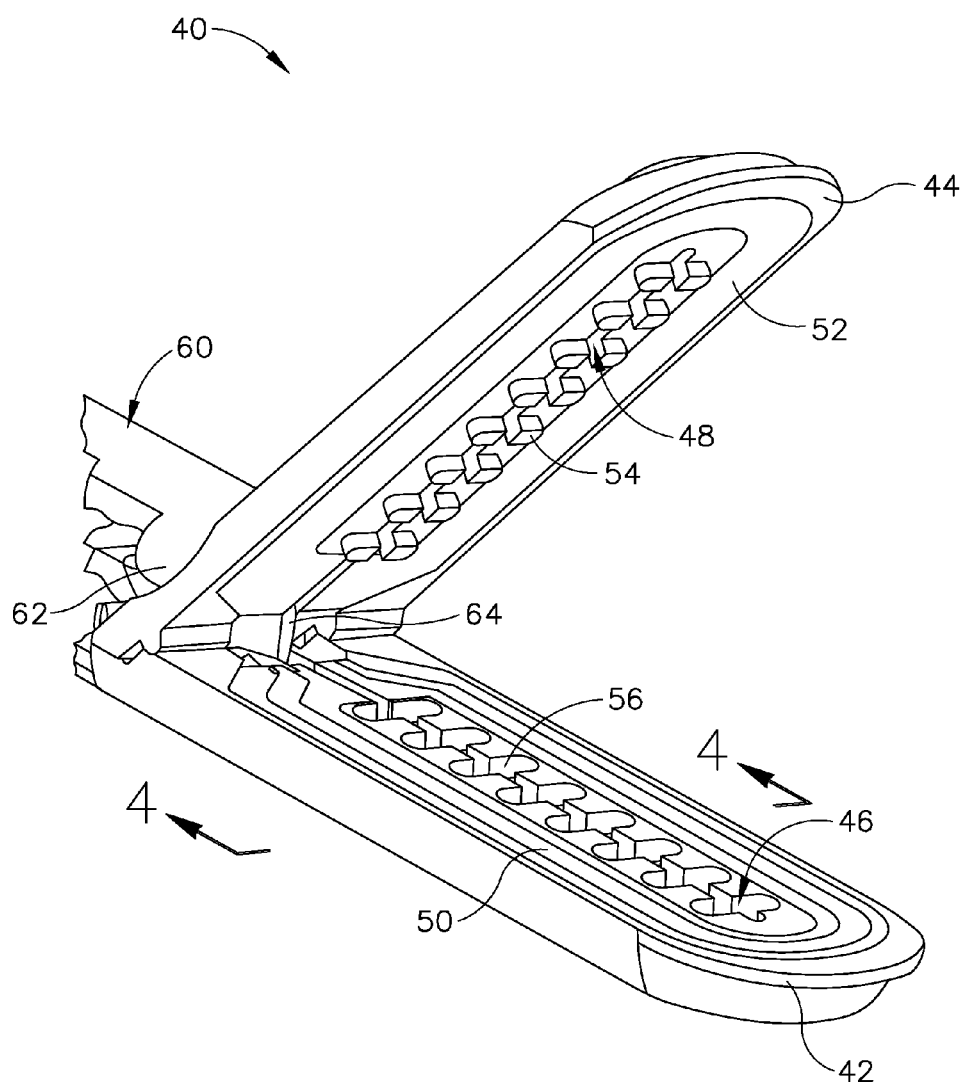
FIG. 3 depicts another perspective view of the end effector of the instrument of FIG. 1, in an open configuration.
Figure 4:
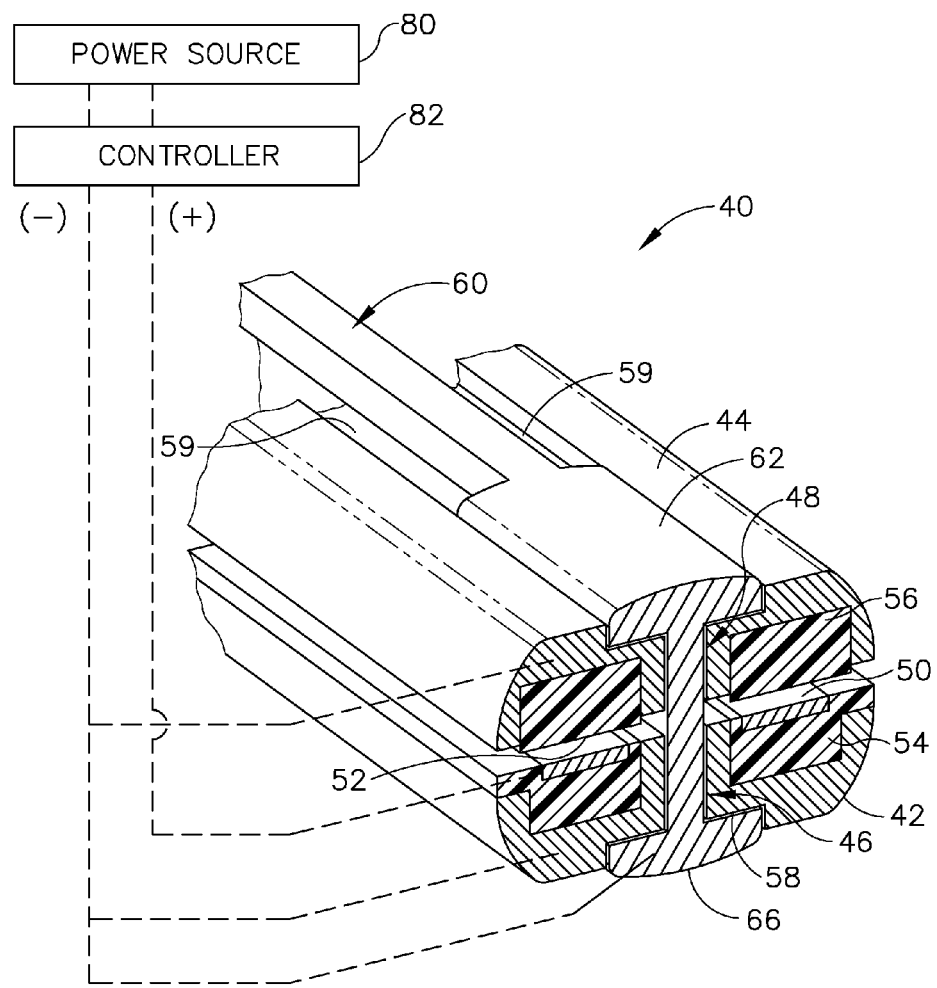
FIG. 4 depicts a cross-sectional end view of the end effector of FIG. 2, taken along line 4-4 of FIG. 3, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar.

Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Electrode Sleeve

It will be understood that in some instances, before or after instrument (10) is used to weld or seal layers of tissue between jaws (42, 44), it may be desirable to further weld or seal portions of tissue outside of jaws (42, 44). Such sealing may halt bleeding in a particular region or otherwise simply be used to connect portions of tissue. For instance, the user may desire that the welded portion may need to be larger in order to ensure a proper seal. In some instances, perhaps the initial firing of instrument (10) did not provide sufficient welding or was unable to weld a portion of tissue that the user desired to have welded. In other instances, the surgical area may be bleeding in a manner in which sealing the tissue would stop or diminish the bleeding. Such bleeding may be adjacent or otherwise separate from tissue transected by blade (64).

Figure 5:
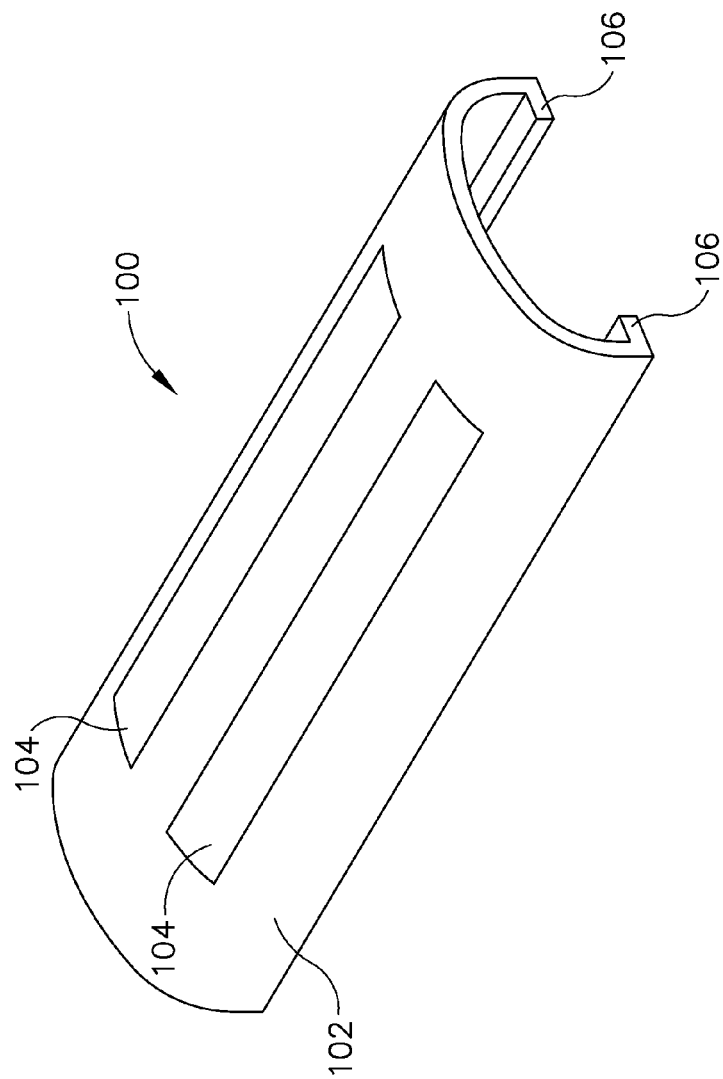
FIG. 5 depicts a perspective view of an exemplary electrode sleeve.
Figure 6:
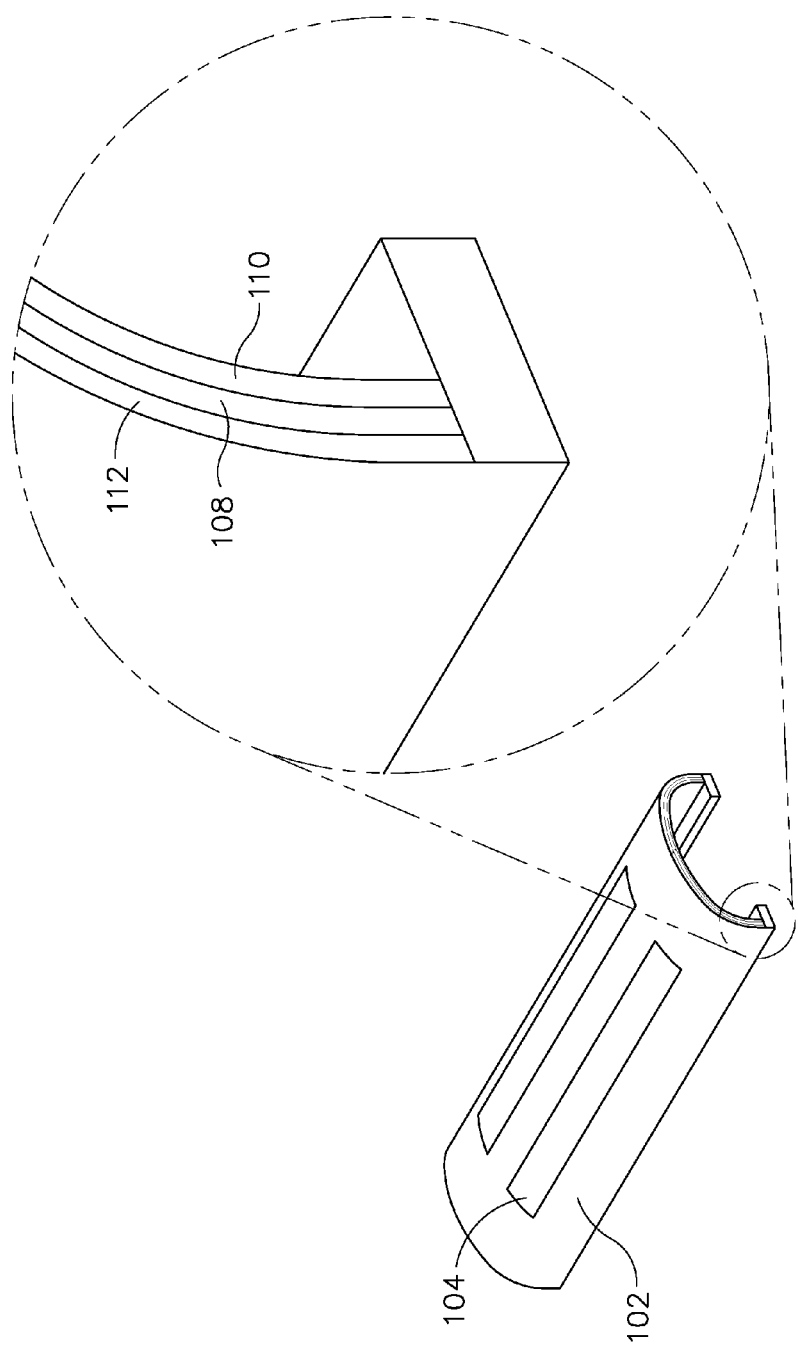
FIG. 6 depicts an enlarged view of the electrode sleeve of FIG. 5 showing the electrode sleeve layers.
Figure 7:
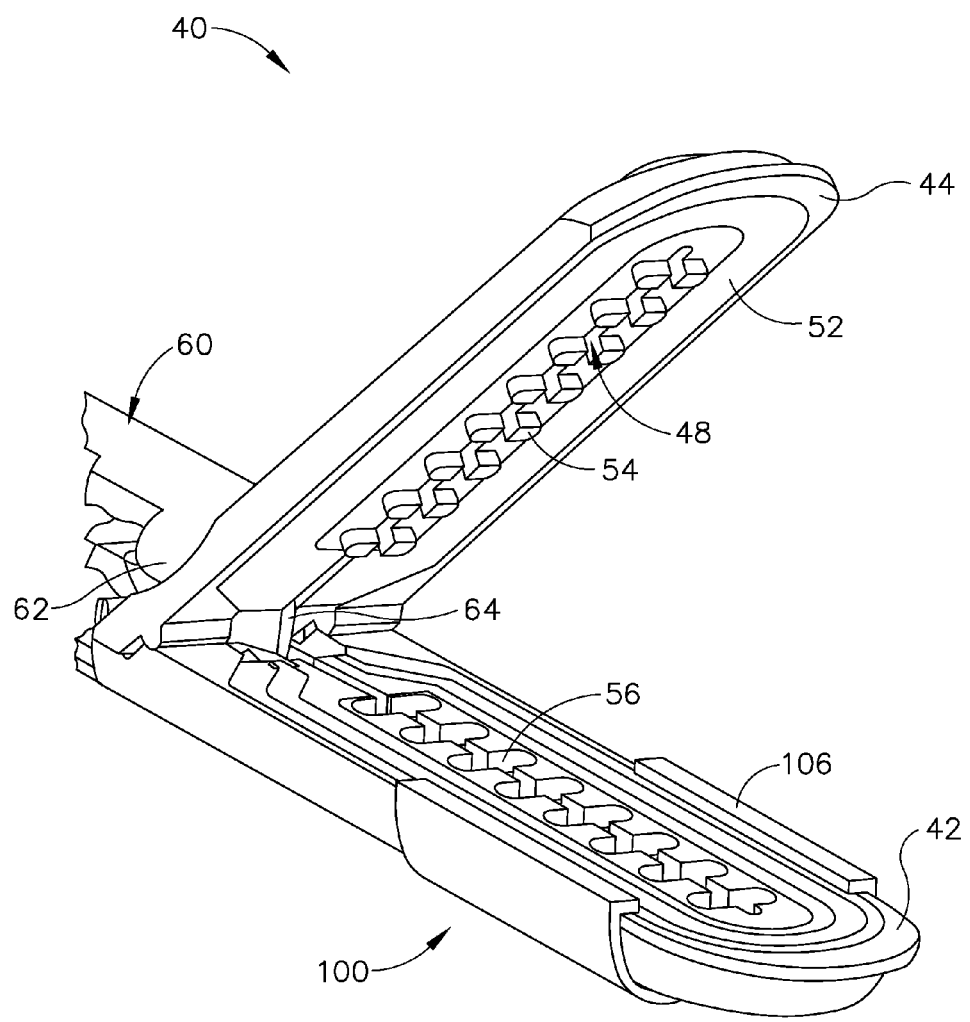
FIG. 7 depicts a perspective view of the electrode sleeve of FIG. 5 engaging the first jaw of an end effector.

FIGS. 5-7 show an exemplary electrode sleeve (100) for use with jaw (42) of instrument (10). In general, electrode sleeve (100) is operable to weld an area of tissue by fitting electrode sleeve (100) over jaw (42), energizing electrode sleeve (100), and subsequently pressing sleeve (100) against a desirable tissue site that the user wishes to weld.

Electrode sleeve (100) comprises a body (102) and electrodes (104). Body (102) includes a pair of opposing longitudinal lips (106), which will be described in further detail below.

Body (102) of electrode sleeve (100) has an elongated, curved shape. In particular, body (102) complements the shape of jaw (42). It will be appreciated that body (102) may have any suitable shape as would be apparent to one of ordinary skill in the art in view of the teachings herein. Furthermore, while in the illustrated version, body (102) is operable to fit on lower jaw (42), it will be understood that body (102) may be shaped to fit on upper jaw (44) as well. In yet other versions, body (102) of electrode sleeve (100) may be operable to fit on either jaw (44) or jaw (42). FIG. 6 shows an enlarged view of a portion of body (102) such that the layers of body (102) are shown. In particular, an insulating layer (110) comprises an insulating plastic film or other suitable insulating layer. While the exemplary version uses a plastic layer, it will be understood that any material suitable for electrically insulating body (102) may be used as would be apparent to one of ordinary skill in the art in view of the teachings herein. Furthermore, an inner layer (108) is made of copper or aluminum or any other suitable conductive material. Inner layer (108) may further comprise a portion of titanium coupled with the copper or aluminum. In the alternative, however, it will be understood that a portion or layer of titanium need not necessarily be used. Inner layer (108) is in electrical communication with electrodes (104) or alternatively may be merely an extension of electrodes (104) into body (102). For instance, heat sink layer (112) may have openings exposing portions of inner layer (108) to form electrodes (104) or in other instances, electrodes (104) may be in contact with inner layer (108) through such openings in heat sink layer (112). Body (102) further includes a heat sink layer (112), which may comprise a plastic or other suitable heat absorbable material. It will be understood that the process of sealing tissue, which will be described further below, may result in it the generation of heat at or around a tissue site. Heat sink layer (112) may be operable to draw heat away from the area of tissue where heat is being generated thereby minimizing thermal spread to adjacent tissue.

Longitudinal lip (106) of body (102) is operable to grasp jaw (42) as seen in FIG. 7. Longitudinal lip (106) complements jaw (42) such that body (102) may be slid over jaw (42) as seen in FIG. 7 with longitudinal lip (106) guiding body (102) onto jaw (42). In the exemplary version, longitudinal lip (106) includes a continuous lip that extends along a substantial portion of length of jaw (42), but it will be understood that longitudinal lip (106) may have any suitable structure for applying and retaining body (102) onto jaw (42). For instance, longitudinal lip (106) may include separated clips along the length of jaw (42) or any other suitable variation. Furthermore, longitudinal lip (106) and body (102) may be shaped such that electrode sleeve (100) forms a frictional fit with jaw (42). As a result, once applied to jaw (42), electrode sleeve (100) does not easily fall off. Body (102) may be resilient, enabling deformation to clip onto jaw (42) transversely; yet maintaining a grip on jaw (42) once clipped on.

Electrodes (104) extend longitudinally along electrode sleeve (100). Electrodes (104) of the exemplary version have a rectangular shape, but it will be understood that electrodes (104) may have any suitable shape. For instance, electrodes (104) may have a square, circular, curved (e.g. sinusoidal) elliptical, or any other suitable shape as would be apparent to one of ordinary skill in the art in view of the teachings herein. While the exemplary version shows two electrodes (104), it will be understood that any suitable number of electrodes may be used as would be apparent to one of ordinary skill in the art in view of the teaching herein. In some versions, electrodes (104) are provided in order to provide localized application of bipolar RF energy. In some other versions, one or more electrodes (104) provide monopolar RF energy. Those of ordinary skill in the art will recognize that monopolar versions may require a ground pad to be placed underneath the patient, a ground patch adhered to the skin of the patient, or some other ground return path feature. In either case, electrodes (104) are operable to apply a current to an area of tissue to effectively weld the tissue.

It will be understood that electrodes (104) may be in communication with power source (80) and controller (82), which are shown in FIG. 2 such that power source (80) can supply current to electrodes (104). In other versions, it will be understood that electrodes (104) may be separately powered. Electrodes (104) may be in electrical communication with power source (80) via a direct, dedicated wire or wires (not shown). In addition to, or in the alternative, electrodes (104) may be in communication with power source (80) via inner layer (108). For instance, inner layer (108) may have openings operable to expose inner layer (108) to electrode surface (50). In other versions, a portion of inner layer (108) may be exposed near longitudinal lips (106), which may be operable to contact electrode surface (50). In some versions, electrodes (104) may be powered through inductive coupling. In yet other exemplary versions, engaging jaw (42) with electrode sleeve (100) may concurrently engage electrical contacts (not shown) on the underside portion of jaw (42), thereby providing electrical communication between power source (80) and electrodes (104). Electrodes (104) may be selectively powered such that when jaws (42, 44) are clamping, or distal blade (64) (shown in FIG. 2) advances to cut tissue, or first and second electrode surfaces (50, 52) (shown in FIG. 3) seal tissue, electrodes (104) are not energized. Thereafter, power source (80) may deliver energy to electrodes (104) for further welding tissue or providing a touch up of bleeding areas of tissue. It will be understood that in some instances, electrodes (104) may be covered or coated with dielectric grease. It will be appreciated that use of dielectric grease may be operable to prevent degradation of electrodes (104), which may otherwise occur over extended use of electrodes (104).

In one exemplary use, electrode sleeve (100) may be applied to jaw (42) of instrument (10) as shown in FIG. 7. In particular, the user may manually slide electrode sleeve (100) onto jaw (42). The user may then connect electrode sleeve (100) to power source (80) or in the alternative, it will be understood that simply sliding electrode sleeve (100) onto jaw (42) establishes the electrical communication between power source (80) and electrode sleeve (100).

Upon engaging jaw (44) with electrode sleeve (100), the user may use instrument (10) to clamp, cut, and seal tissue as described above. Thereafter, if the user wishes to weld other portions of tissue, the user may then press sleeve (100) against the tissue that the user desires to weld. Controller (82) may then instruct power source (80) to supply current to electrode sleeve (100). Thereafter, bipolar RF current flows through tissue between electrodes (104), thereby welding the tissue. It will be understood that controller (82) may be manually controlled or be operable to provide electrode sleeve (100) with current when tissue comes into contact with electrodes (104). For instance, it may be understood that contact with tissue or other electrically conductive material may close the circuit between electrodes (104), thereby initiating the flow of current. Other suitable variations may be used for initiating the flow of current to electrodes (104) as would be apparent to one of ordinary skill in the art in view of the teachings herein. Thereafter, the user may move end effector (40) to other portions of tissue to weld or may simply end the procedure.

It should also be understood that, in addition to or in lieu of the foregoing, electrode sleeve (100) may be configured in accordance with at least some of the teachings of U.S. patent application Ser. No. 13/709,473, entitled "Bipolar Electrosurgical Features for Targeted Hemostasis," filed on even date herewith, published as U.S. Pub. No. 2014/0163541 on Jun. 12, 2014, the disclosure of which is incorporated by reference herein. Various suitable ways in which the teachings herein may be combined with various teachings in that reference will be apparent to those of ordinary skill in the art.

III. Exemplary Energy Sensitive Electrode Sleeve

Figure 8:
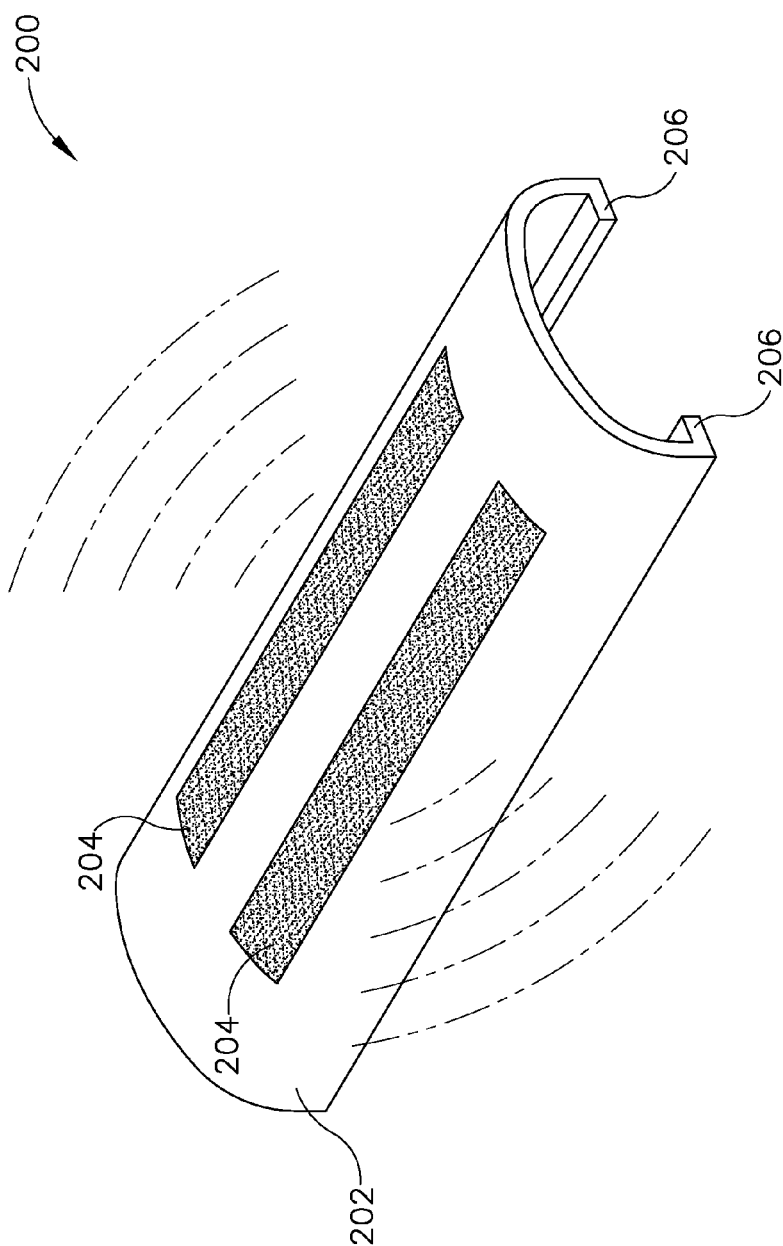
FIG. 8 depicts a perspective view of the exemplary electrode sleeve of FIG. 5 with an energy sensitive coating being energized.

As discussed above, as tissue is being welded, areas around tissue and end effector (40) along with electrodes (104) may generate heat. It will be understood that it may be desirable to know whether electrodes (104) are in a heated state. FIG. 8 shows an exemplary electrode sleeve (200) having a body (202), longitudinal lips (206), and electrodes (204). It will be understood that electrode sleeve (200) is substantially similar to electrode sleeve (100) described in FIG. 5. Electrodes (204) are coated with an energy sensitive material such that when electrodes (204) are energized, electrodes (204) change color to convey to the user that electrodes (204) are energized. For instance, when energized, electrodes (204) may turn red, orange, yellow, blue, or any other color suitable to indicate to the user that electrodes (204) are in an energized state.

Electrodes (204) may be energy sensitive in a variety of different ways. For instance, electrodes (204) may be operable to be sensitive to electricity, heat, or any other suitable indicator operable to allow a user to know that electrodes (204) are energized. In some versions, electrodes (204) may be coated with an energy sensitive paint. In yet other versions, electrodes (204) may be constructed of an energy sensitive material or may incorporate a layer of energy sensitive material. For instance, electrodes (204) may comprise energy sensitive liquid crystals, paint, labels, pigments, inks, or any other suitable energy sensitive material. Examples of energy sensitive paints include paints made by Thermographic Measurement, Ltd., Lakbriek Korthals BV, TIP Temperature Products, Inc., B+H Colour Change Ltd., Hallcrest Inc., and Thermochromatic Color-Changing Paint. In yet other versions, electrodes (204) may comprise or be coated with a phosphorescent material such that electrodes (204) illuminate as electrodes (204) are exposed to energy. It will be understood, however, that any suitable energy sensitive feature may be used as would be apparent to one of ordinary skill in the art in view of the teachings herein.

In some versions as discussed above, electrodes (204) may be operable to depict an energized or un-energized state. However, it will be understood that electrodes (204) may be operable to show incremental changes in electrode (204) state as well. For instance, electrodes (204) may have an initial state of green. As electrodes (204) begin to heat up, electrodes (204) may turn yellow. As electrodes (204) progressively heat up, electrodes (204) may progressively change color to indicate that electrodes (204) are becoming hotter and hotter. For example, after turning yellow, once electrodes (204) continue to heat, electrodes (204) may turn orange and then red to indicate the most heated or energized state of electrodes (204). As a result, it will be appreciated that the user may observe if electrodes (204) are a little bit heated or extremely hot. Other desirable information may be gathered based on the heated state of electrodes (204). For instance, the heat level of electrodes (204) may indicate when sealing of tissue is or near complete, whether tissue is being overcooked, whether adjacent tissue is receiving too much heat, and whether electrodes (204) are in fact working and delivering energy to the surgical site. Furthermore, it may be appreciated that electrodes (204) need not necessarily heat or energize uniformly. As a result, electrodes (204) may be operable to show what portions of electrodes (204) are hotter than others, which may provide useful information to the user.

Figure 9:
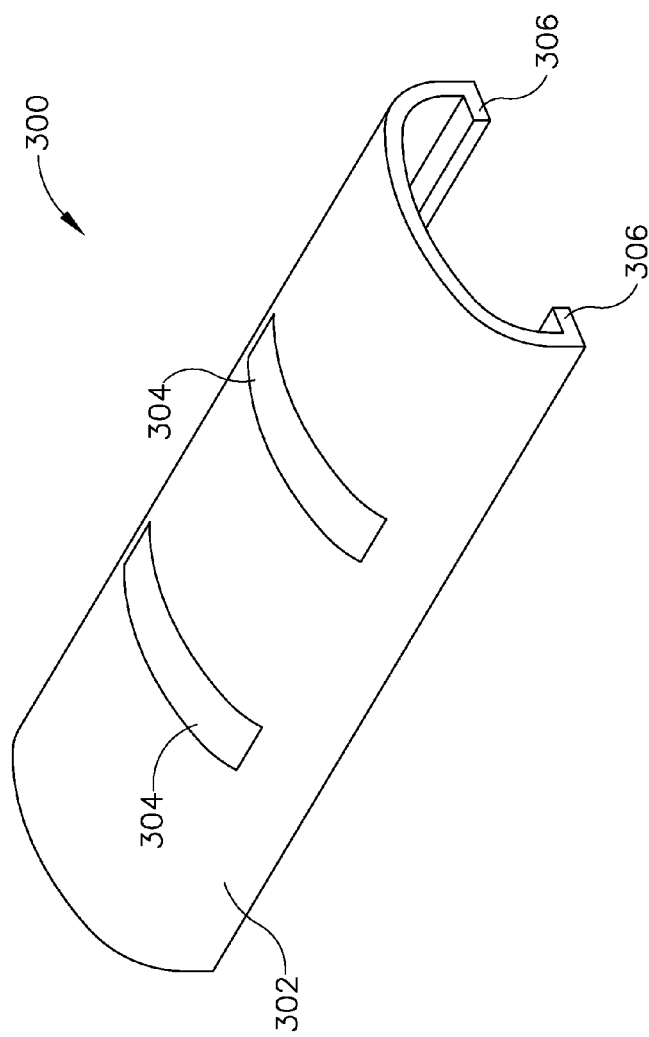
FIG. 9 depicts a perspective view of an alternative exemplary electrode sleeve having an alternative electrode shape.
Figure 10:
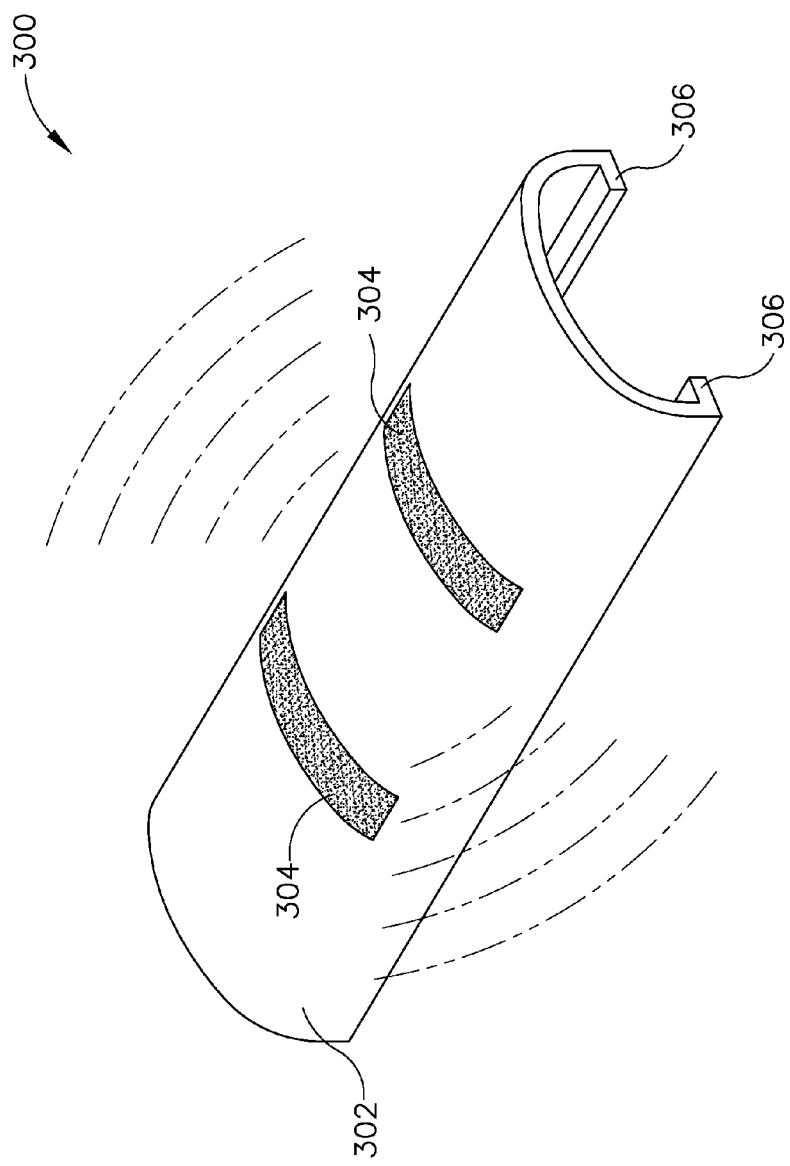
FIG. 10 depicts a perspective view of the exemplary electrode sleeve of FIG. 9 with an energy sensitive coating being energized.

FIGS. 9-10 show yet another exemplary version of an electrode sleeve (300) with a body (302), longitudinal lips (306), and electrodes (304). It will be understood that electrode sleeve (300) is in many ways substantially similar to electrode sleeve (200) shown in FIG. 8. In the version shown in FIGS. 9-10, electrodes (304) extend transversely across electrode sleeve (300). It will be understood that electrodes (304) may be positioned in any suitable orientation across body (302) of electrode sleeve (300) and other suitable orientations will be apparent to one of ordinary skill in the art in view of the teachings herein.

FIG. 9 shows electrode sleeve (300) in an un-energized state, and FIG. 10 shows electrode sleeve (300) in an energized state, indicating to the user that electrodes (304) are energized by changing color of electrodes (304).

Figure 11:
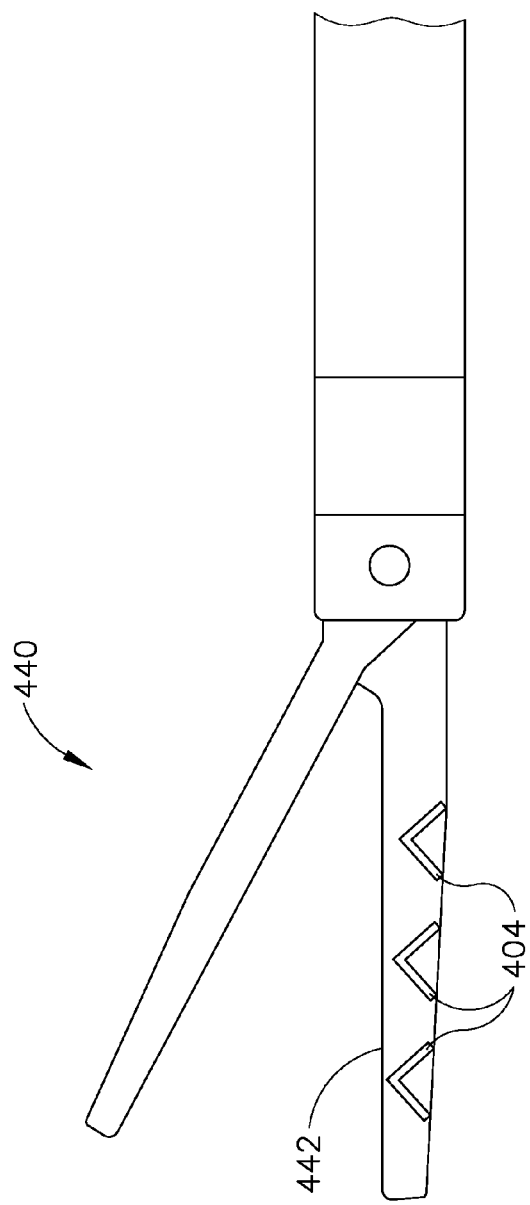
FIG. 11 depicts a side view of an alternative exemplary end effector having an energy sensitive region integrated into the end effector.
Figure 12:
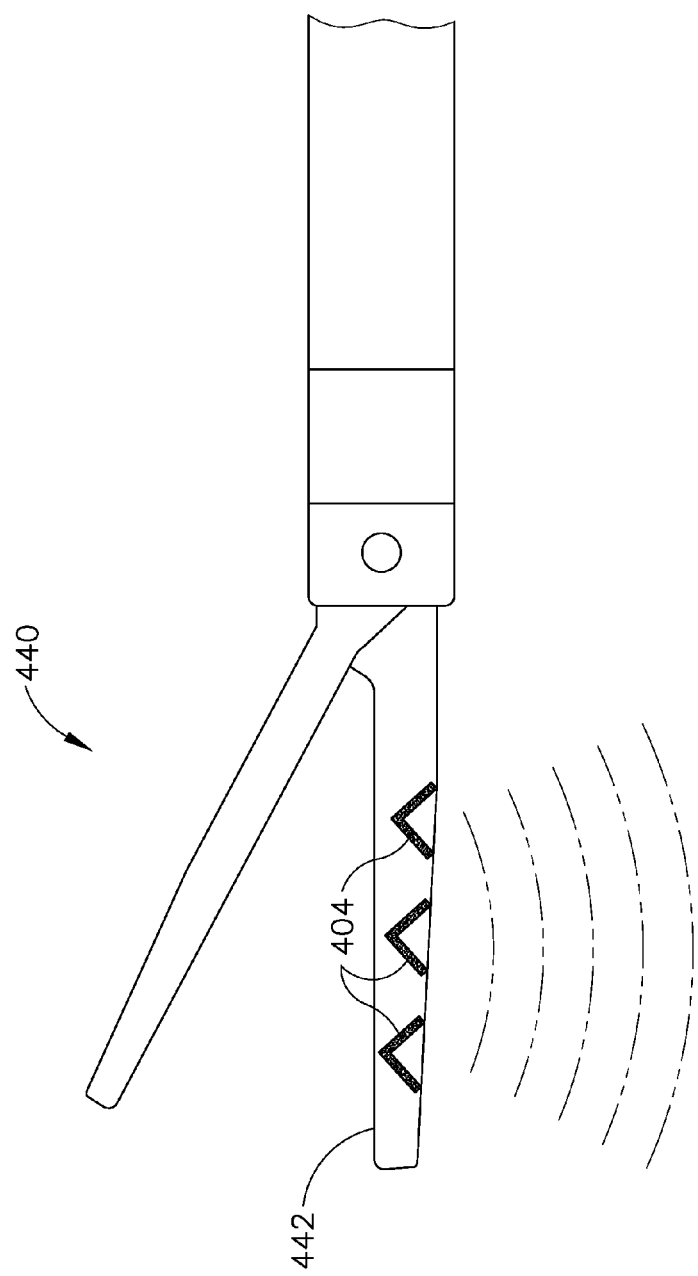
FIG. 12 depicts a side view of the end effector of FIG. 11 being energized.

It will be understood that in some instances, it may be desirable for the user to know if a portion of the end effector is energized, rather than simply knowing if electrode sleeve (300) is energized. FIGS. 11-12 show yet another exemplary version of an end effector (440) outfitted with an energy sensitive region (404). It will be understood that end effector (440) is substantially similar to end effector (40) shown in FIG. 1. In particular, jaw (442) lacks an external electrode in this example. It will be understood that energy sensitive region (404) may be operable to change color or otherwise change its appearance in response to end effector (440) being energized. As discussed above with respect to electrodes (204, 304), energy sensitive regions (404) of end effector (440) may be painted, coated with, or constructed using an energy sensitive material as discussed above with respect to electrodes (204, 304) (e.g. phosphorescent materials, etc.). As a result, as a user uses end effector (440) at a surgical site and end effector (440) becomes heated through use, energy sensitive regions (404) of end effector (440) change color, as shown in FIG. 12, such that the user will know that end effector (440) has become heated. It should be understood that energy sensitive region (404) may provide visual feedback indicating the energization status of end effector (40) regardless of whether energy sensitive region (404) itself is able to apply energy to tissue. Similarly, electrodes (204, 304) may be configured to provide visual feedback indicating the energization status of end effector (40) regardless of whether electrodes (204, 304) are themselves able to apply energy to tissue.

As seen in the exemplary version, energy sensitive region (404) may be shaped as three diamonds curved upwards around jaw (442) of end effector (440) such that a user can see energy sensitive region (404) from looking at the side of end effector (440). While the exemplary version shows three diamonds as the general shape of energy sensitive region (404) it will be understood that any suitable shape may be used for energy sensitive region (404). Furthermore, it will be understood that any suitable number of energy sensitive regions (404) may be used as would be apparent to one of ordinary skill in the art. For instance, one, three, or more regions may be used. Finally, while the exemplary version shows energy sensitive region (404) located on jaw (442), it will be understood that energy sensitive region (404) may be positioned at any portion of end effector (440) suitable to inform the user that a relevant portion of end effector (440) has been heated or otherwise energized. It will also be understood that energy sensitive regions (404) may be used in conjunction with electrode sleeve (200, 300) such that in addition to or in the alternative, energy sensitive regions (404) can assist the user in determining which portions of end effector are heated or otherwise energized. Positioning energy sensitive regions (404) on end effector (440) also enables surgeon to see the energized status within the surgical field of view. For instance, if the surgeon is viewing an endoscope image viewing screen, the surgeon does not need to look away from the screen to receive real-time visual feedback indicating that end effector (440) is energized.

It should also be understood that, in addition to or in lieu of the foregoing, electrode sleeves (200, 300) may be configured in accordance with at least some of the teachings of U.S. patent application Ser. No. 13/709,473, entitled "Bipolar Electrosurgical Features for Targeted Hemostasis," filed on even date herewith, published as U.S. Pub. No. 2014/0163541 on Jun. 12, 2014, the disclosure of which is incorporated by reference herein. Various suitable ways in which the teachings herein may be combined with various teachings in that reference will be apparent to those of ordinary skill in the art.

IV. Exemplary Feedback System for Surgical Instrument

As discussed above, in some instances, it may be desirable for the user to know when portions of end effector (40) have become heated or otherwise energized. Accordingly, it will further be appreciated that in addition to or in the alternative of the ways of informing the user about the heated state of end effector (40), it may be desirable to detect other changes of instrument (10), which was shown in FIG. 1. Furthermore, it may be desirable to inform the user of such a change in ways different than a color changing material as was discussed with respect to FIGS. 8-12.

Figure 13:
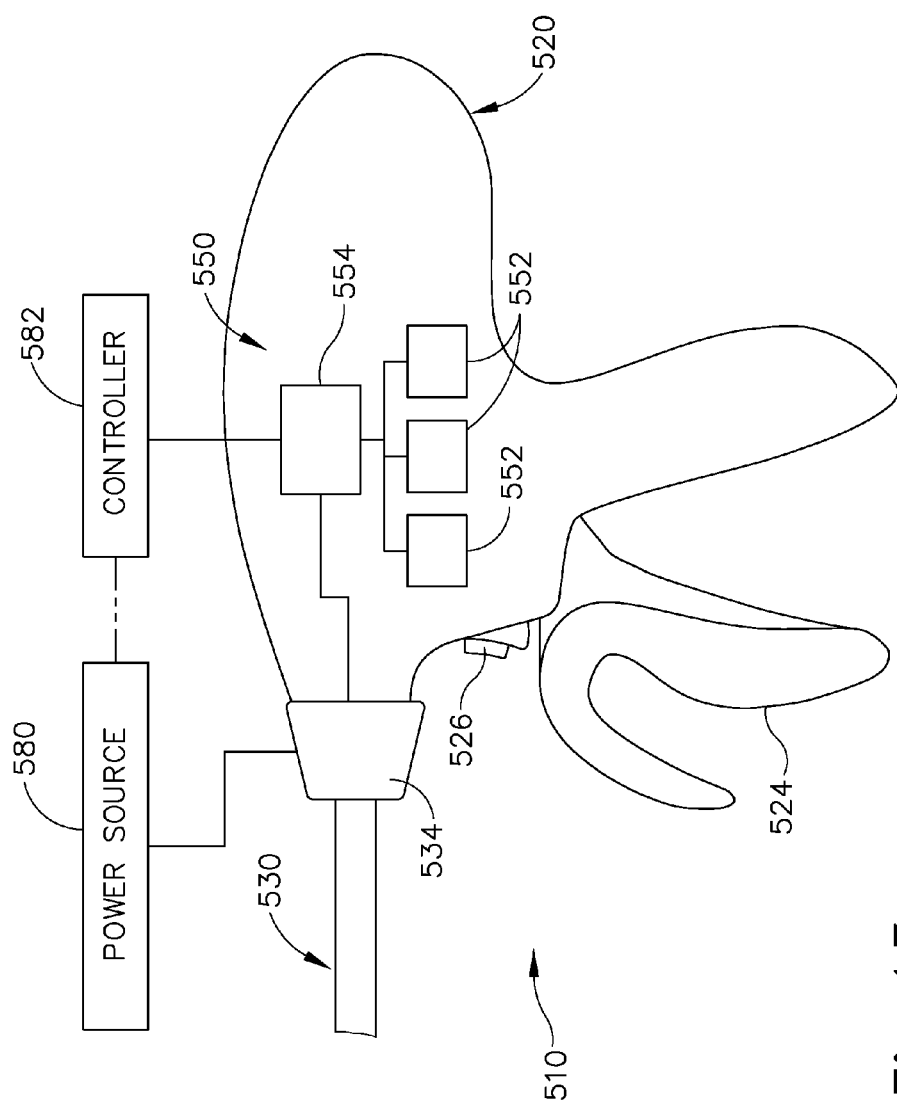
FIG. 13 depicts a cross sectional side view of an exemplary handpiece with an exemplary feedback system within the handpiece.

FIG. 13 shows an exemplary instrument (510) operable generally to cut and weld tissue. It will be understood that instrument (510) is a variation of instrument (10) of FIG. 1. Instrument (510) comprises a handpiece (520), a shaft (530) extending from handpiece (520), a trigger (524) with an activation button (526), and a knob (534). Instrument (510) further comprises an exemplary feedback system (550) within handpiece (520). Instrument (510) is also in electrical communication with controller (582) and power source (580). It will be understood that power source (580) and controller (582) are substantially similar to power source (80) and controller (82) of FIG. 2.

Feedback system (550) comprises a feedback controller (554) and signal devices (552). Generally speaking, feedback system (550) is operable to detect an operational change or detect a measurable change in instrument (510) as instrument (510) is being used. Feedback system (550) may be operable to detect any particular kind of change or measurement. Thereafter, feedback system (550) is operable to provide feedback to the user to indicate that change. For instance, the feedback may be visually similar to the color changing behavior of electrodes (304) of FIG. 10, which was discussed above. In addition to or in the alternative, the feedback may be in the form of a haptic feedback or an audible feedback. Indeed, any feedback suitable to inform the user of a change within instrument (510) may be conveyed to the user. While feedback system (550) is shown with instrument (510), it will be understood that such feedback system (550) may be directly used with instrument (10) or other suitable instruments for which a user may wish to monitor particular metrics of the instrument. The feedback mechanism will be discussed in further detail below.

Feedback controller (554) is in communication with controller (582) and end effector (not shown in FIG. 13) of instrument (510). Feedback controller (554) may further be in contact with one or more sensors that are located on controller (582) and that are operable to detect various changes within instrument (510) conveyed through controller (582) or by directly detecting such changes through direct communication with sensors. Furthermore, feedback controller (554) is in communication with the end effector of instrument (510) and other parts of instrument such as controller (582) such that feedback controller (554) can determine the general states of operation of instrument (510). For instance, feedback controller (554) is in communication with controller (582) to determine whether power is being applied by power source (580). Indeed, feedback controller (554) may comprise any suitable sensor operable to monitor any aspect of instrument (510) by simply establishing connection between feedback controller (554) and the portion of instrument (510) to be monitored.

Furthermore, feedback controller (554) is in communication with signal devices (552). In the exemplary version, three signal devices (552) are used, but it will be understood that any suitable number of signal devices (552) may be used as would be apparent to one of ordinary skill in the art in view of the teachings herein. For example, a single device, two, or more than three devices may be used to convey to the user the states of various aspects of instrument (510). Signal devices (552) are operable to provide any suitable type of perceivable feedback for the user. For example, signal devices (552) may produce haptic feedback, visual feedback, and/or auditory feedback that the user may feel, see, or hear.

With respect to haptic feedback, signal devices (552) are positioned in the handpiece (520) such that if a detectable change is observed, the signal devices (552) may be operable to provide a vibration that the user can feel through handpiece (520). Since the user is typically grasping handpiece (520) during use, it will be understood that the user may feel the vibration produced by signal devices (552) through handpiece (520). Haptic feedback may be provided in numerous ways. By way of example only, vibrations may be continuous, progressive, or be provided at the end of operations to indicate status. For instance, handpiece (520) may vibrate whenever power is applied to electrodes (50, 52). As another merely illustrative example, vibrations may increase in intensity and/or frequency (or decrease in intensity and/or frequency) in response to changes in tissue impedance detected at electrodes (50, 52). As yet another merely illustrative example, handpiece (520) may produce a single vibration to indicate the end of a cutting stroke (e.g., when firing beam (60) reaches a distal-most position). Other suitable vibration schemes will be apparent to those of ordinary skill in the art in view of the teachings herein.

Regarding audio feedback, signal devices (552) may emit a sound upon the occurrence of some perceivable event. The sound produced by signal devices (552) may include a beep, buzzer, high pitched chirp, or any other audible signal that may indicate to the user a particular state or action of instrument (510). Regarding visual feedback, signal devices (552) may produce colors, images, lights, or any combination thereof to indicate to the user a change within instrument (510). While the above means of signaling to the user including haptic, audio, and visual feedback are discussed separately, it will nevertheless be understood that the above feedback mechanisms may be used separately or in combination with each other. Furthermore, while the illustrated version shows three signal devices (552), it will be understood that any suitable number of signal devices (552) may be used. Signal devices (552) also need not be located within handpiece (520).

As discussed above, establishing communication between feedback controller (554) and different portions of instrument (510) can be used to detect any perceivable changes in instrument (510) or stages or operation during use of instrument (510). As a result, feedback controller (554) may be operable to detect if any portion of instrument (510) has malfunctioned. Furthermore, feedback controller (554) could monitor initialization tests prior to using instrument (510) in a surgical procedure, or feedback controller (554) could be used monitor how various components within instrument (510) actuate. Other suitable measurable aspects may be monitored by feedback controller (554). Thereafter, upon determining that a particular change has occurred, such as instrument (510) malfunction, feedback controller (554) may direct signal devices (552) to alert the user through haptic, audio, and/or visual feedback.

By way of example, a user may turn on instrument (510). Feedback controller (554), which is in communication with different portions of instrument (510), determines that all components are in working order. Feedback controller (554) directs signal devices (552) to indicate to the user that instrument (510) is in working order. For instance, a green light may indicate that instrument (510) is ready for use. Thereafter, the user may use instrument (510) to clamp, cut, and weld a portion of tissue in a similar manner to the use of instrument (10) shown in FIGS. 1-4. Since feedback controller (554) is in contact with the end effector of instrument (510), it will be understood that feedback controller (554) can detect when various stages of operation have occurred. For instance, when the jaws clamps down on tissue (similar to jaws (42, 44) of FIG. 2), feedback system (550) may provide a haptic vibration to the user to indicate that proper clamping has occurred. Furthermore, once a distal blade (similar to distal blade (64) of FIG. 2) fires, feedback system (550) may further provide a different haptic vibration to indicate to the user that the distal blade has fired. As welding of tissue occurs by providing energy via power source (580), feedback system (550) can also provide yet a different haptic vibration or perhaps an audio cue that welding has occurred. Signal devices (552) may even indicate to the user that the end effector is in a heated state, which the user accordingly may use to determine how to proceed with the procedure. In some instances, instrument (510) may be equipped with electrode sleeve (100) shown in FIG. 5, which may allow the user to provide touch up tissue welding to the surgical area. Furthermore, electrode sleeve (100) may be in communication with feedback controller (554) as well such that the user may be informed of the operation and state of electrode sleeve (100) during use. While the above description depicts one merely exemplary use of feedback system (550), it will be understood that other suitable procedures for using feedback system (550) with instrument (510) to provide the user with useful data may be used as would be apparent to one of ordinary skill in the art in view of the teachings herein.

V. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
    (a) a body configured to mechanically couple with a portion of an end effector;
    (b) a lip in communication with the body, wherein the lip is configured to grip a portion of the end effector; and
    (c) at least one electrode in communication with the body, wherein the at least one electrode is configured to weld at least a portion of tissue using electrical energy.

2. The apparatus of claim 1, wherein the body has an elongated curved shape configured to complement contours of an end effector.

3. The apparatus of claim 1, wherein the lip has an elongated edge configured to run along the length of an end effector.

4. The apparatus of claim 1, wherein the at least one electrode is oriented longitudinally along the body.

5. The apparatus of claim 1, wherein the at least one electrode is configured to turn off when the end effector is in operation.

6. The apparatus of claim 1, wherein the body further comprises a heat sink layer.

7. The apparatus of claim 1, wherein the body further comprises an insulating layer comprising a plastic film.

8. The apparatus of claim 1, wherein at least a portion of the at least one electrode comprises an energy sensitive material.

9. The apparatus of claim 8, wherein the energy sensitive material is configured to change color upon the application of energy to the at least one electrode.

10. The apparatus of claim 8, wherein the energy sensitive material is configured to be heat sensitive.

11. The apparatus of claim 8, wherein the energy sensitive material is configured to be sensitive to electrical current flowing through the at least one electrode.

12. The apparatus of claim 1, further comprising a feedback system in communication with the body, wherein the feedback system comprises a feedback controller and at least one signal device, wherein the feedback controller is configured to detect changes in at least one measurable characteristic of the end effector.

13. The apparatus of claim 12, wherein the feedback controller of the feedback system is operable to detect whether electrical current is flowing through the at least one electrode.

14. The apparatus of claim 13, wherein the at least one signal device is configured to provide haptic feedback to the user upon current flowing through the at least one electrode.

15. The apparatus of claim 13, wherein the at least one signal device is configured to provide audio feedback to the user upon current flowing through the at least one electrode.

16. An apparatus comprising:
(a) a handpiece;
(b) an end effector in communication with the handpiece, wherein the end effector comprises a first and second jaw, wherein the end effector is configured to clamp, cut, and seal tissue; and
(c) an energy sensitive region, wherein the energy sensitive region is positioned on a portion of the end effector, wherein the energy sensitive region is configured to alter the energy sensitive region's visual appearance in response to the application of energy to the end effector.

17. The apparatus of claim 16, wherein the energy sensitive region is configured to be heat sensitive.

18. The apparatus of claim 16, wherein the energy sensitive region is configured to change color upon the application of energy to the energy sensitive region.

19. An apparatus comprising:
(a) a handpiece;
(b) an end effector in communication with the handpiece, wherein the end effector is configured to clamp and cut tissue;
(c) a feedback controller in communication with the end effector, wherein the feedback controller is configured to detect at least one aspect of the end effector; and
(d) a signal device in communication with the feedback controller, wherein the signal device is configured to inform a user of a change in the at least one aspect of the end effector, wherein the signal device is positioned within the handpiece.

20. The apparatus of claim 19, wherein the signal device is configured to provide a haptic, audible, or visual feedback to the user.

\* \* \* \* \*